(12) United States Patent
Krishnan et al.

(10) Patent No.: US 10,589,724 B2
(45) Date of Patent: Mar. 17, 2020

(54) STOWABLE VEHICLE SENSOR

(71) Applicant: Ford Global Technologies, LLC, Dearborn, MI (US)

(72) Inventors: Venkatesh Krishnan, Canton, MI (US); Andre Sykula, Sterling Heights, MI (US); Segundo Baldovino, Novi, MI (US); Jose Garcia Crespo, Bloomfield Township, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 218 days.

(21) Appl. No.: 15/647,487

(22) Filed: Jul. 12, 2017

(65) Prior Publication Data
US 2019/0016306 A1    Jan. 17, 2019

(51) Int. Cl.
| | |
|---|---|
| B60S 1/08 | (2006.01) |
| B60S 1/56 | (2006.01) |
| G05D 1/02 | (2020.01) |
| G01N 21/15 | (2006.01) |
| G02B 27/00 | (2006.01) |

(52) U.S. Cl.
CPC .......... *B60S 1/0848* (2013.01); *B60S 1/0822* (2013.01); *B60S 1/56* (2013.01); *G01N 21/15* (2013.01); *G02B 27/0006* (2013.01); *G05D 1/024* (2013.01); *G05D 1/0257* (2013.01); *G01N 2021/151* (2013.01)

(58) Field of Classification Search
None
See application file for complete search history.

(56) References Cited

U.S. PATENT DOCUMENTS

| | | | |
|---|---|---|---|
| 6,527,000 B1 | 3/2003 | Randmae et al. | |
| 7,965,336 B2 * | 6/2011 | Bingle | B60R 11/04 348/374 |
| 2006/0068696 A1 | 3/2006 | Ashford et al. | |
| 2015/0040953 A1 * | 2/2015 | Kikuta | B60S 1/52 134/123 |

FOREIGN PATENT DOCUMENTS

| | | |
|---|---|---|
| DE | 202006017665 U1 | 3/2007 |
| EP | 2003471 A1 | 12/2008 |
| JP | 20173541 A | 1/2017 |
| WO | 2016008722 A1 | 1/2016 |

* cited by examiner

*Primary Examiner* — Rita P Adhlakha
(74) *Attorney, Agent, or Firm* — Frank A. MacKenzie; Bejin Bieneman PLC

(57) ABSTRACT

A sensor cleaning system for a vehicle is disclosed that includes a sensor assembly. The sensor assembly may include a fluid-dispensing nozzle for a vehicle sensor, a housing within a body of a vehicle, and a driving member which can move the nozzle between a stowed position within the housing and a deployed position.

10 Claims, 11 Drawing Sheets

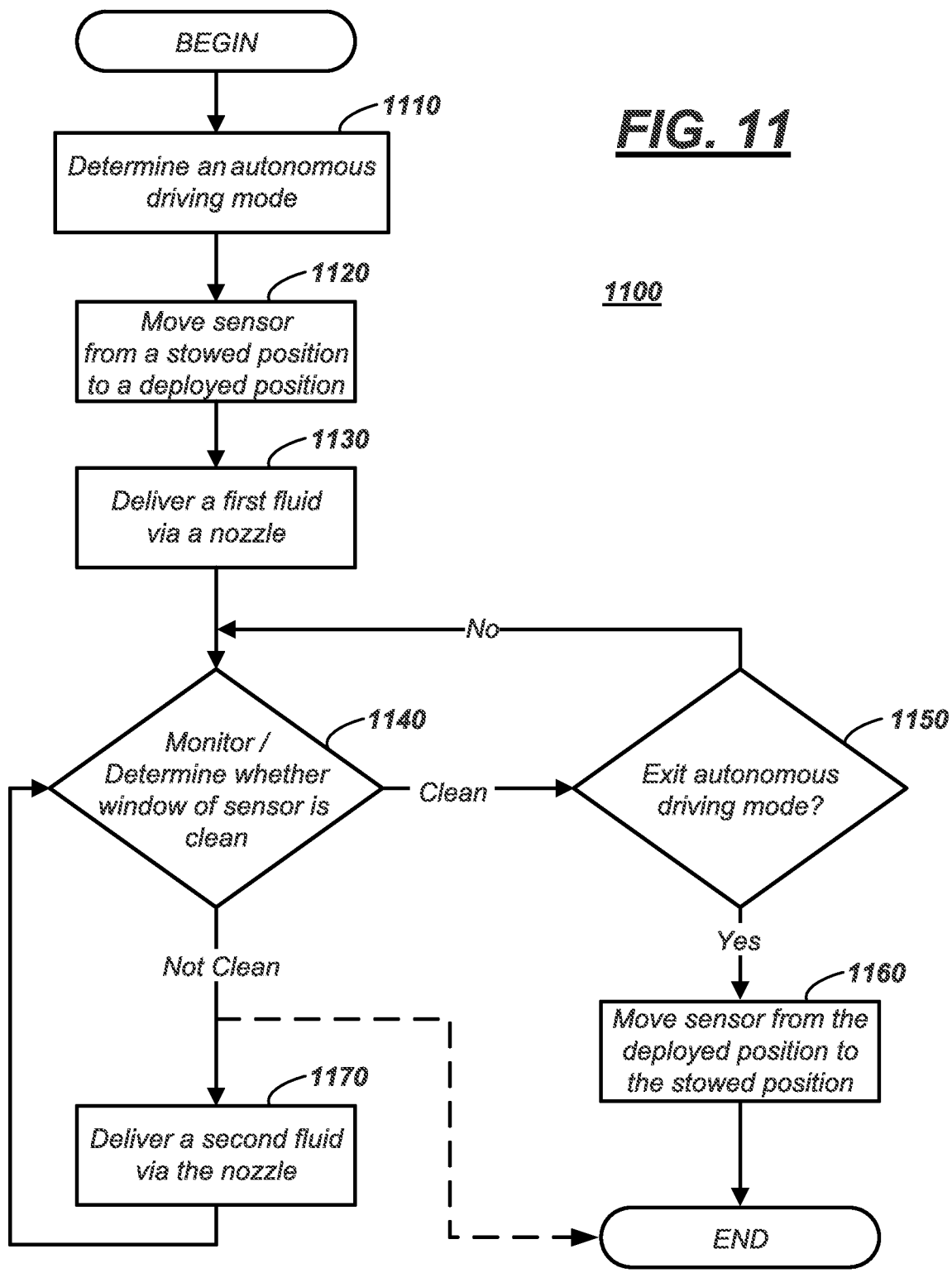

STOWABLE VEHICLE SENSOR

BACKGROUND

Cleaning a vehicle exterior may occur in a variety of ways. Users of the vehicle may hand-wash the vehicle at home or power-wash the vehicle at a so-called do-it-yourself station. Or the vehicle may be driven through a so-called automated car wash facility. For example, in the automated car wash, a machine having a nozzle is located proximate to the vehicle; thereafter, a soap and water mixture may be applied to the vehicle exterior, and a series of brushes on the machine may remove dirt and debris. The machine further may rinse and blow-dry the vehicle.

BRIEF DESCRIPTION OF THE DRAWINGS

FIG. 11 is a flow diagram illustrating a process for cleaning the sensor shown in FIGS. 8-10.

DETAILED DESCRIPTION

Figure 1:
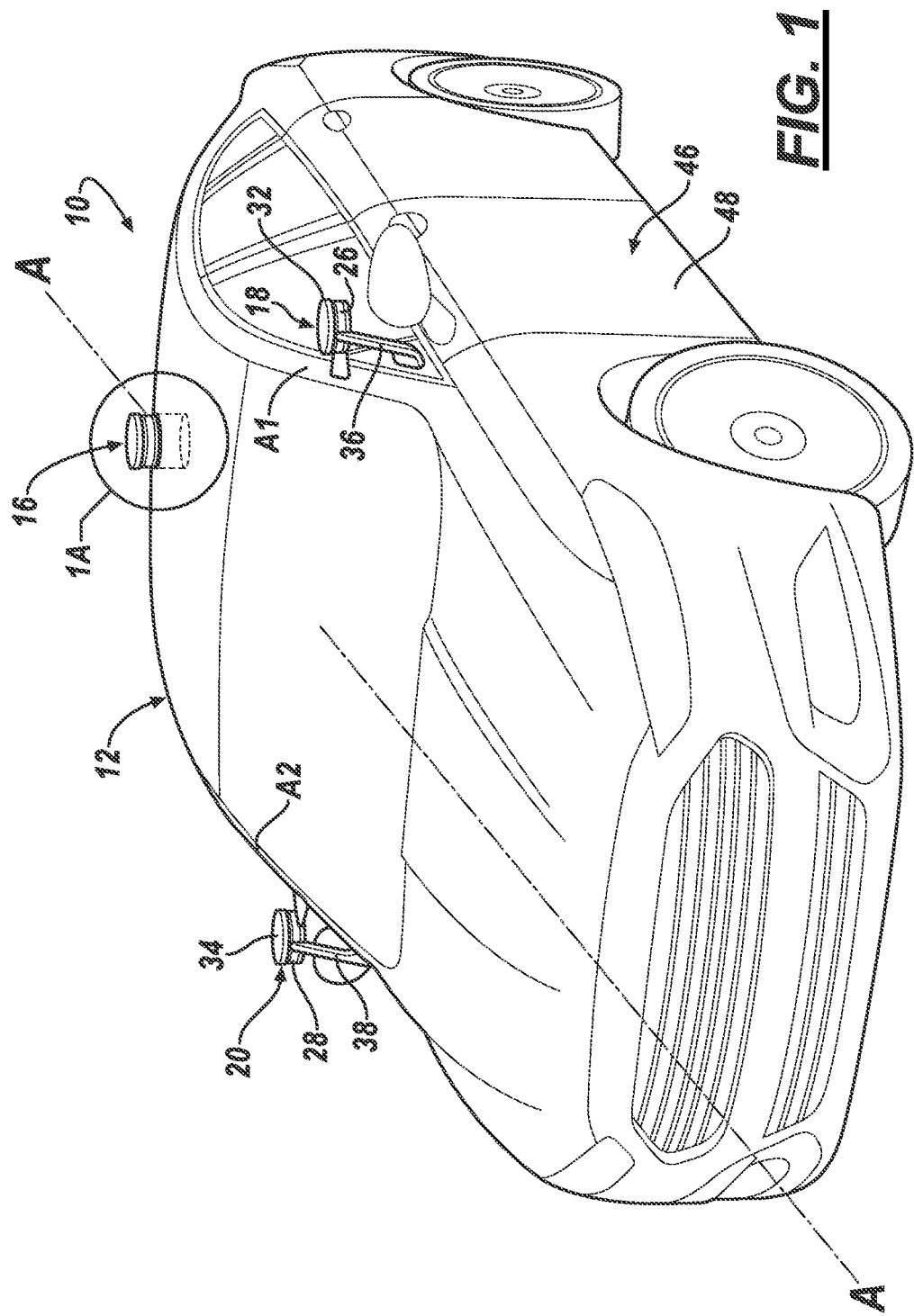
FIG. 1 is a perspective view of autonomous vehicle having a sensor cleaning system.

According to an illustrative example, a sensor cleaning system for a vehicle is described that includes a sensor assembly. The sensor assembly may include a fluid-dispensing nozzle for a vehicle sensor, a housing within a body of a vehicle, and a driving member which can move the nozzle between a stowed position within the housing and a deployed position.

According to one illustrative example, the assembly includes: a housing having a cavity sized for a sensor, the housing comprising an opening at a first end, and a housing base having a drain at an opposite end; a sensor mount; and a driving member coupled to the mount to move the mount, through the opening, between a stowed position and a deployed position.

According to the at least one example set forth above, the assembly further may include an annular nozzle for the sensor positioned above the base so that fluid dispensed by the nozzle exits the cavity via the drain.

According to the at least one example set forth above, the driving member comprises a screw coupled to a motor.

According to the at least one example set forth above, the drive includes an outer sleeve and an inner sleeve that is coupled to the mount and, when the mount moves between the stowed and deployed positions, the inner sleeve moves relative to the outer sleeve.

According to the at least one example set forth above, the housing base is sloped toward the drain.

According to the at least one example set forth above, the assembly further may include the sensor coupled to a nozzle and the mount.

According to the at least one example set forth above, the assembly further may include: a nozzle, for the sensor, that is sized to move through the opening, wherein the nozzle comprises: a first member comprising an annular first flange extending radially-inwardly from a first nozzle base; and a second member having an annular second flange extending radially-outwardly from a second nozzle base, the first and second flanges forming a circumferential passage and an at least partially circumferential outlet.

According to the at least one example set forth above, at least a portion of the first flange is parallel to at least a portion of the second flange.

According to the at least one example set forth above, a width of the outlet is uniform.

According to the at least one example set forth above, the first or second member comprises a circumferentially-extending wall protruding from the respective first or second nozzle base, wherein the wall is located inboard of the second flange, wherein an edge of the wall abuts the respective second or first nozzle base.

According to another example, a system is disclosed that includes: a sensor assembly that includes: a sensor; an annular nozzle carried by the sensor; a housing within a body of a vehicle; a driving member which moves the sensor and nozzle between a stowed position within the housing and a deployed position.

According to the at least one example set forth above, the system further may include a first pump and at least one passage for delivering fluid from the pump to the nozzle.

According to the at least one example set forth above, the system further may include a second pump, wherein the first pump delivers a first fluid via a first passage and the second pump delivers a second fluid via a second passage, wherein the first and second fluids are different.

According to the at least one example set forth above, the system further may include a computer programmed to control the first pump and receive data from the sensor.

According to the at least one example set forth above, the system further may include a computer; and a plurality of sensors each having an annular nozzle, wherein the computer is programmed to receive data from each of the plurality of sensors.

According to the at least one example set forth above, the sensor is a light detection and ranging (LIDAR) device.

According to the at least one example set forth above, the nozzle comprises: a first member comprising an annular first flange extending radially-inwardly from a first base; and a second member having an annular second flange extending radially-outwardly from a second base, the first and second flanges forming a circumferential passage and an at least partially circumferential outlet.

According to the at least one example set forth above, the first or second member comprises a circumferentially-extending wall protruding from the respective first or second base, wherein the wall is located inboard of the second flange, wherein an edge of the wall abuts the respective second or first base.

According to another example, a method is disclosed that includes: actuating a driving member to move a sensor, coupled to a nozzle, from a first position within a housing on a vehicle, to a second position, at least partially outside the housing; and delivering a fluid to the nozzle to clean the sensor.

According to the at least one example set forth above, the method further may include actuating a pump to deliver the fluid, wherein, actuation of the pump, results in dispensing an arcuate fluid blade from the nozzle to an outer surface of the sensor.

Figure 1A:
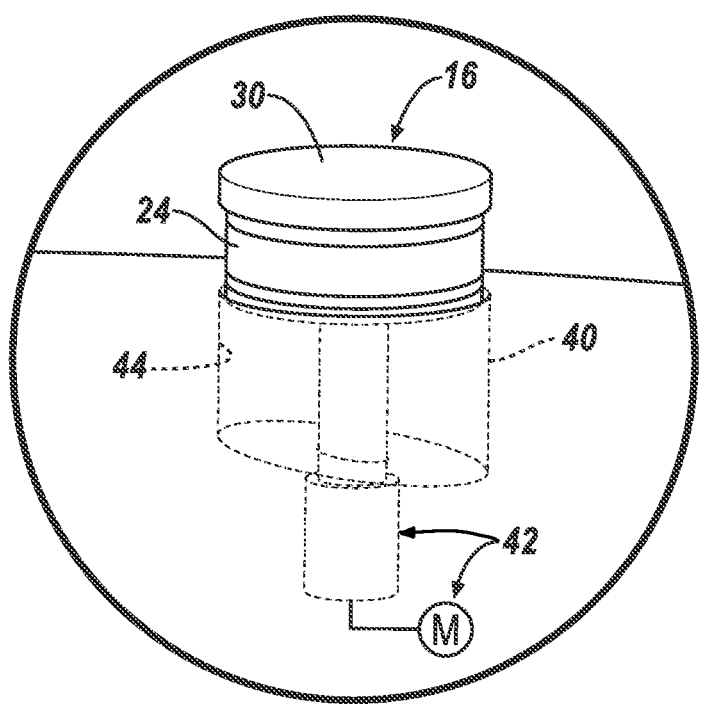
FIG. 1A is an enlarged view of a portion of FIG. 1, illustrating a sensor assembly in greater detail.
Figure 2:
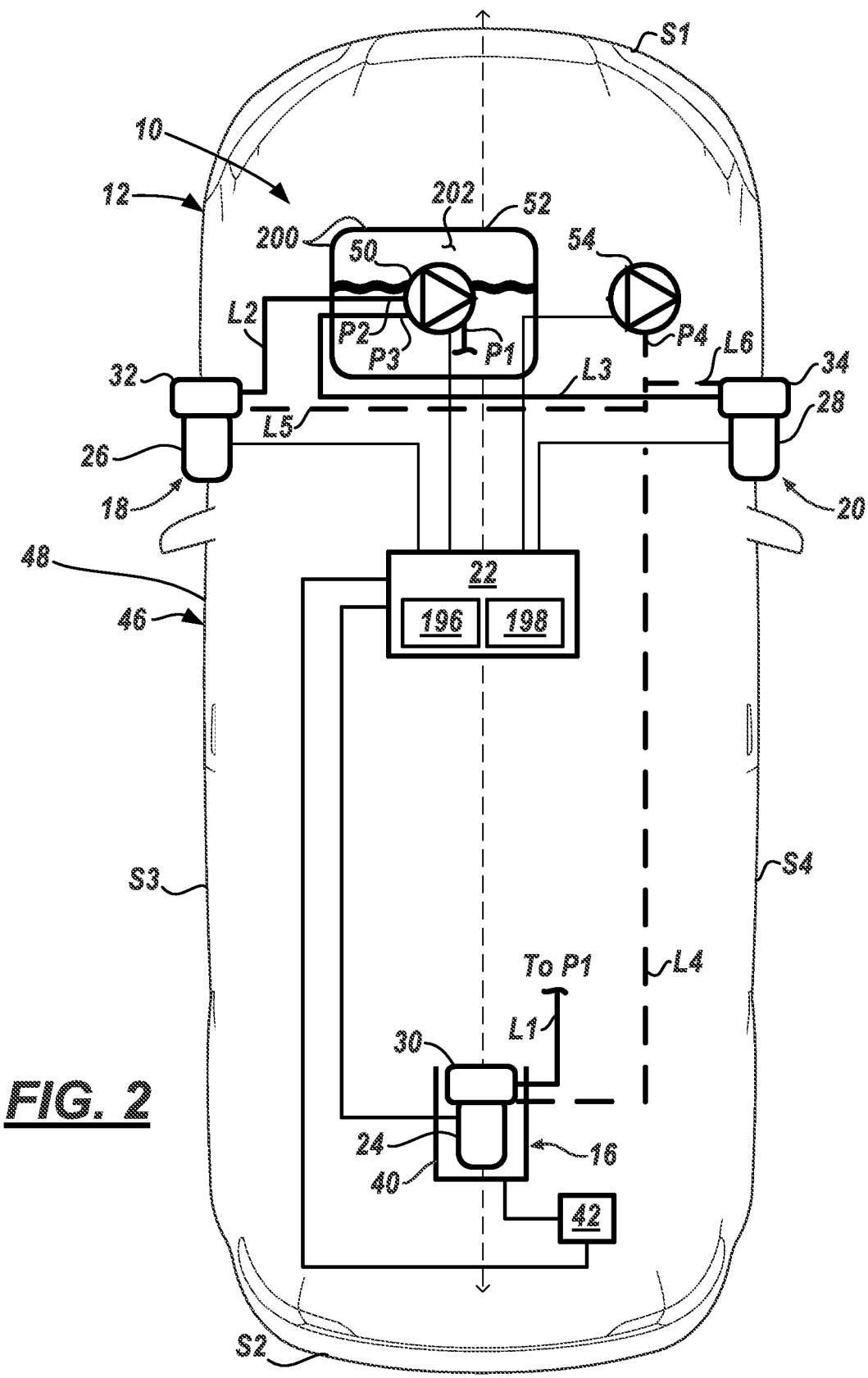
FIG. 2 is a schematic view of a sensor cleaning system of the vehicle shown in FIG. 1.

Now turning to the figures, wherein like numerals indicate like parts throughout the several views, there is shown a sensor cleaning system 10 for a vehicle 12 (e.g., see FIGS. 1, 1A, 2). As an example, the system 10 may include at least one sensor assembly 16 (e.g., three are shown (16, 18, 20) for purposes of illustration) and an onboard computer 22 programmed to control and/or communicate with the sensor assemblies 16-20 and other aspects of the sensor cleaning system. Sensor assemblies 16-20 may comprise a sensor 24, 26, 28 (respectively) and respective fluid-dispensing nozzles 30, 32, 34. The sensors 24-28 may provide data to computer 22 which may be used for operating the vehicle 12 in a fully autonomous mode, and the nozzles 30-34—which may be coupled to a respective upper end of sensors 24-28—may be used to clean an outer surface of the respective sensor. According to one example, sensor assemblies 18-20 respectively may include a port-side bracket 36 and a starboard-side bracket 38 to support the respective sensors 26, 28 near or via vehicle A-pillars A1, A2 (as shown). And according to at least one example, assembly 16 further may comprise a housing 40 and a driving member 42 that moves the sensor 24 and nozzle 30 between a stowed position (within a cavity 44 of the housing 40) and a deployed position (at least partially outside of housing 40 and cavity 44). As will be explained in greater detail below, sensor 24 and nozzle 30 may be stowed within the housing 40 at times to minimize the collection of debris on sensor 24 (e.g., when the sensor 24 is not being used).

The vehicle 12 is shown as a passenger car; however, vehicle 12 could also be a truck, sports utility vehicle (SUV), recreational vehicle, bus, train, marine vessel, aircraft, or the like that includes the sensor cleaning system 10. According to at least one example, the vehicle 12 may be operated in any one of a number of autonomous modes using computer 24, (as described more below). For example, vehicle 12 may operate in a fully autonomous mode (e.g., a level 5), as defined by the Society of Automotive Engineers (SAE) (which has defined operation at levels 0-5), as explained more below. In other examples, vehicle may operate at levels 0-2, wherein a human driver monitors or controls the majority of the driving tasks, often with no help from the vehicle 12. For instance, at level 0 ("no automation"), a human driver is responsible for all vehicle operations. At level 1 ("driver assistance"), the vehicle 12 sometimes assists with steering, acceleration, or braking, but the driver is still responsible for the vast majority of the vehicle control. At level 2 ("partial automation"), the vehicle 12 can control steering, acceleration, and braking under certain circumstances without human interaction. In other examples, vehicle may operate at levels 3-4, wherein the vehicle 12 assumes more driving-related tasks. For instance, at level 3 ("conditional automation"), the vehicle 12 can handle steering, acceleration, and braking under certain circumstances, as well as monitoring of the driving environment. Level 3 may require the driver to intervene occasionally, however. At level 4 ("high automation"), the vehicle 12 can handle the same tasks as at level 3 but without relying on the driver to intervene in certain driving modes. And in at least one example, vehicle 12 operates at level 5 ("full automation"), wherein the vehicle 12 can handle all tasks without any driver intervention.

Vehicle 12 may comprise a vehicle body 46 that may be of a unibody construction in which at least some of the body 46 is exposed presenting a so-called class-A surface 48, i.e., a surface 48 specifically manufactured to have a high-quality, finished aesthetic appearance free of blemishes. Alternatively, body 46 may be of a body-on-frame construction, or of any other suitable construction. Regardless, body 46 may be formed of any suitable material, for example, steel, aluminum, etc. As will be described in greater detail below, the body 46 may carry and/or support the sensor assemblies 16-20.

As best shown in FIG. 2, the sensor cleaning system 10 more particularly may include the sensor assemblies 16-20 (e.g., each including a sensor and a nozzle), computer 22, a first fluid pump 50 in a reservoir 52, a second fluid pump 54, and a plurality of supply passages L1, L2, L3, L4, L5, L6. As described briefly above, each sensor 24-28 may be coupled to a nozzle for cleaning the respective sensor. According to at least one example, each sensor 24-28 may be similar or identical and each nozzle 30-34 may be similar or identical. Therefore, only one of each will be described below.

Turning now more particularly to FIGS. 3-7, sensor 24 may comprise a shell 60 having a top 62, a bottom 64, and at least one circumferentially-extending side 66 extending between the top 62 and bottom 64—the top 62, bottom 64, and side(s) 66 collectively defining an interior volume (not shown). The illustrated shell 60 is shaped as a right cylinder; however, this is not required. For example, shell 60—and more particularly side 66—may have different shapes (e.g., non-limiting examples include an at least partially circular cylinder, an at least partially elliptic cylinder, an at least partially ovoid shape, an at least partially parabolic cylinder, an at least partially hyperbolic cylinder, an at least partially angular or multi-faceted shape, or the like). In addition, the shape of the shell 60 may be oblique, rather than right.

Shell 60 may carry an optically-transmissive window 68 (e.g., comprised of glass, acrylic, etc.) and a panoramic sensing element (not shown; e.g., a so-called detector, imaging engine, imaging core, or the like). An exterior surface 70 of window 68 at least partially circumferentially extends around side(s) 66. And in at least one example, a contour of the window 68 follows the shape of the shell 60 (e.g., the shape of window 68 also may be cylindrical). In other examples, window 68 may be otherwise curved or even at least partially angular (e.g., elliptical, parabolic, faceted, etc., as described above).

While not shown, it should be appreciated that the panoramic sensing element may be positioned within the shell 60 and relative to an inner surface (not shown) of window 68 so that the sensing element may receive and/or focus light and/or other radiation onto one or more detecting surfaces thereof. In this manner, the sensing element may provide imaging data from the vehicle's surroundings to one or more computing devices (e.g., such as computer 22)—thereby enabling computer 22 to control vehicle 12 in a fully autonomous or other autonomous mode. In some examples, the panoramic sensing element mechanically rotates within the shell 60, relative to the window 68. In other examples, the sensing element is fixed within the shell 60—e.g., the detecting surface(s) of the sensing element being positioned and oriented to suitably receive light and/or radiation through window 68.

The shell 60 may have any suitable size. According to one example, the shell 60 has a circular diameter less than five (5) inches and a height less than four (4) inches. Further, in one example, window 68 is circular having a diameter less than five (5) inches and a height that is less than two (2) inches—the window 68 circumferentially extending around the entirety of side 66—enabling the sensor 24 to have up to a 360° field of view (FOV).

According to one example, sensor 24 is a light detection and ranging (LIDAR) device. One non-limiting commercial implementation is the VLP-16 by Velodyne LiDAR, Inc. However, this is merely an example and is not required. Sensor 24 also could be a charge-coupled device (CCD) camera, a complementary metal-oxide semiconductor (CMOS) camera, a near infrared (NIR) device (e.g., operating in 0.74-1 micrometer (μm) range), a thermal imaging or forward-looking infrared (FLIR) device (e.g., operating in the short (1-3 μm), medium (3-5 μm), or long (8-14 μm) ranges), or the like. Also, in some examples, sensor 24 could be a LIDAR device while sensors 26 and/or 28 could be different types of sensors (or vice-versa); however, in at least one example, sensors 24-28 are all LIDAR devices. In yet other examples, vehicle 12 may comprise only one or two sensor assemblies—or in other examples, it may comprise more than the three illustrated sensor assemblies 16-20.

Turning now to a description of nozzle 30 coupled to sensor 24, nozzle 30 may comprise a two-piece (or two-part) design; e.g., nozzle 30 comprises a first or upper member 80 coupled to a second or lower member 82 to form a passage 84 which receives fluid from the first and/or second pump 50, 54 and delivers the fluid to the surface 70 of sensor window 68 via an at least partially circumferential outlet 88. Upper member 80 comprises a base 90, a circumferential flange 92 extending from one side 94 (e.g., lower side) of the base 90 (e.g., shown downwardly), and a port element 96 located on the flange 92 which forms at least part of the inlet 86.

The base 90 may be flat, and its shape and size may correspond to the shape of the sensor shell 60. For example, where the top 62 of sensor 24 is circular, the base 90 also may be circular; however, this is merely an example (and is not required in all examples). A diameter of the base 90 may be larger than the top 62 of sensor 24 so that fluid dispensed from the outlet 88 may travel downwardly along the side(s) 66 thereof. The base 90 also may have a through-hole 98 extending from an upper side 100 of the base 90 to the lower side 94 thereof (e.g., and in one example, the hole 98 may be centered, located along a longitudinal axis B of nozzle 30). In one example, a boss 102 (along axis B) comprising a circumferentially-extending wall may protrude from the lower side 94 for positioning the upper member 80 relative to the lower member 82; however, the boss is not required. The hole 98 may be located within the boss 102, as illustrated.

Flange 92 may be adapted to form a portion of the passage 84—e.g., when coupled to lower member 82, as described below. The flange 92 may extend both axially (from the lower side 94) and radially inwardly with respect to axis B terminating at an edge 104. An angle formed between an inner surface 106 of the flange 92 and the base 90 may be suitable to direct fluid flow toward surface 70 of window 68 (e.g., non-limiting examples include an angle measuring 45°-90°). According to one example, the larger the diameter of the base 90, the smaller the angle may be—e.g., such that when the diameter of the base 90 is marginally larger than the diameter of the sensor top 62 (e.g., 5-10% larger), the angle may be 80°-90°.

Port element 96 may be adapted to direct fluid into the passage 84 formed by the upper and lower members 80, 82 thereby promoting a circumferential fluid-flow direction 110 within the respective nozzle 30 (e.g., here a counterclockwise fluid-flow direction is shown (from the top views); however, the port element 96 could be arranged to promote a clockwise fluid-flow direction instead). In at least the illustrated example, port element 96 protrudes radially outwardly of flange 92 and may comprise a ramp portion 112 and a receptacle portion 114. The ramp portion 112 includes an outer wall 116 that may extend radially-outwardly from an outer surface 118 of flange 92 at a first region 120. The ramp portion 112 may extend circumferentially and radially-outwardly from the first region 120 to a second region 122 that is adjacent the receptacle portion 114 (e.g., having any suitable slope or curvature) (e.g., the first region 120 being arcuately spaced from the second region 122). In the illustration, the ramp portion 112 extends gradually radially outwardly in a clockwise direction (e.g., from a top view); however, this is merely one example. Ramp portion 112 further may comprise an upper wall 124 and a lower wall 126. The upper wall 124 may be comprise a radially-outwardly extension of base 90—e.g., extending to the outer wall 116. The lower wall 126 may extend from the flange edge 104 to the outer wall 116. Thus, outer, upper, and lower walls 116, 124, 126 may direct fluid received from an end 128 of passage L1 into the passage 84, as described more below.

Receptacle portion 114 may include a first wall 130 and a second wall 132 arranged to define a cavity 134 sized to receive the end 128 of the passage L1. More particularly, first wall 130 may extend circumferentially from the outer wall 116 in the clockwise direction to the second wall 132 (from the top view)—and the second wall 132 may extend radially inwardly adjoining the outer surface 118 of flange 92 at a third region 136 (e.g., wherein the third region 136 is arcuately spaced from both the first and second regions 120, 122). Accordingly, the cavity 134 may be defined by an inner surface 138 of the first wall 130, an inner surface 140 of the second wall 132, and a third wall 142 which extends inwardly from the first wall 130 to the flange edge 104. The third wall 142 may include a coupler 144 adapted to receive the end 128 of passage L1. According to one example, the coupler 144 includes an opening 146 sized to receive end 128. The third wall 142 is optional; e.g., the passage end 128 may be press-fit within the cavity 134 so as to direct fluid directly into the ramp portion 112, or the coupler 144 could be attached to any suitable part or surface of the upper member 80, or the like.

Turning now to the lower member 82, the lower member 82 may include a base 150, a circumferential wall 152 extending from an upper side 154 of the base 150, and a flange 156 extending radially outwardly of the wall 152 and axially with respect to the upper side 154. The base 150 may be flat, and its shape and size also may correspond to the shape of the sensor shell 60. For example, where the window 68 of sensor 24 is cylindrical, the base 150 may be circular; however, this is merely an example (and is not required in all examples). In addition, a lower side 160 of base 150 may be located adjacent the top 62 of sensor 24. The lower side 160 may be flat or have any other suitable shape—e.g., and it may or may not follow the contour of top 62.

A diameter of the base 150 may be larger than (or the same size as) the diameter of sensor 24 but smaller than that of the upper member 80—e.g., in order to direct fluid downwardly along the side(s) 66 thereof (as will be described more below). The base 150 may have a through-hole 158 extending from the upper side 154 of the base 150 to the lower side 160 thereof (e.g., and the hole may be centered along axis B); as will be explained more below, the holes 98, 158 may be aligned so that the upper and lower members 80, 82 of the nozzle 30 may form the passage 84 and outlet 88 and also so that the nozzle 30 may be coupled to the sensor 24.

In one example, a boss 162 (along axis B) comprising a circumferentially-extending wall may protrude from the upper side 154 for positioning the lower member 82 relative to the upper member 80 and the sensor 16; however, the boss 162 is not required. The hole 158 may be located within the boss 162. When assembled, bosses 102, 162 may abut one another as shown and act as spacers. According to at least one example, the boss 162 may serve as an alignment guide for boss 102 during assembly—e.g., the diameter of boss 102 may be larger than that of boss 162 enabling boss 102 to slide over boss 162 (or the diameters could differ enabling boss 162 to slide over boss 102); other examples of bosses 102, 162 are also possible.

The circumferential wall 152 may be located in an outboard region 164 of the base 150 and may extend axially from a surface thereof terminating at an edge 166. When upper and lower members 80, 82 are assembled, edge 166 may abut the lower side 94 of upper member 80. As shown best in FIG. 6, the location of wall 152 relative to side 94 may define a periphery region 167 on the lower side 94 of upper member 80 (e.g., outboard of wall 152), and the region 167 and inner surface 106 of the flange 92 may form a portion of passage 84.

On lower member 82, an interior region 168 may be located inwardly of wall 152—e.g., a volume of the interior region 168 defined by the lower side 94 of upper member 80, an inner surface 170 of the wall 152, the upper side 154 of lower member 82, and the bosses 102 and/or 162. The edge 166 may be press-fit against the lower side 94 of upper member 80 so that this interior region 168 is sealed off from fluid flow within passage 84 (thereby promoting greater fluid pressure at the outlet 88). In one example, the interior region 168 is hollow for weight-saving purposes; however, this is not required.

The flange 156 may be coupled to and extend radially-outwardly from an outer surface 174 of the circumferential wall 152. Flange 156 may comprise an upper surface 178 that extends radially outwardly from surface 174, an edge surface 180, and a lower surface 182—edge surface 180 extending between the upper and lower surfaces 178, 182. In at least one example, the angle formed between the outer and upper surfaces 174, 178 may be less than 90° thereby creating a channel 184 of passage 84 which promotes circumferential fluid flow and circulation.

The edge surface 180 may define a diameter of the lower member 82. In at least one example, the diameter of edge surface 180 is less than a diameter of inner surface 106 (e.g., measured nearer edge 104). And according to one example, at least a portion of edge surface 180 and at least a portion of inner surface 106 may be parallel and oriented to direct fluid flow axially and radially inwardly (e.g., so that fluid may flow down the side(s) 66 of sensor 24).

Collectively, inner surface 106 of flange 92 (upper member 80) and edge surface 180 of flange 156 (lower member 82) define an opening 186 of outlet 88. In at least one example, a width of the opening 186 may be uniform thereby promoting an even delivery of fluid pressure from the outlet 88. According to one example, the circumferential outlet 88 extends entirely around the lower member 80. And according to another example, the circumferential outlet 88 extends partially therearound—e.g., at least 270° (e.g., and the passage L1 is located adjacent the side(s) 66 within a so-called dead-zone of the sensor 24). When mounted to sensor 24, lower surface 182 may extend radially outwardly farther than the side(s) 66 of the shell 60. This is not required however (e.g., the edge surface 180 instead could be flush with the side(s) 66).

As used herein, a dead zone is a region wherein the respective sensor (e.g., the panoramic sensing element) either does not receive imaging data due to its optical configuration (e.g., aperture size and shape, focal parameters, or the like) or it does not receive imaging data due to a shroud, physical obstruction, or other structure (such as one or more fixed vehicle components). Portions of one or more of passages L1-L6 may block part of a respective field of view of the detectors (not shown) of sensors 24-28; consequently, in at least some examples, each sensor 24-28 may have a dead zone (e.g., between 5° and 90°). According to one example, dead zones of sensors 26-28 may be directed toward a longitudinal vehicle centerline axis A of vehicle 12 so that the sensors 26-28 may sense objects forward of and along the sides of vehicle 12, and a dead zone of sensor 24 may be directed vehicle-forwardly so that sensor 24 still may sense objects along the sides of and behind the vehicle 12.

According to at least one example, the inlet 86 of nozzle 20 further includes a notch 190 within flange 156 (of lower member 82), as well as the port element 96 (of upper member 80). For example, the notch 190 may include a circumferential region wherein the flange 156 is absent and the circumferential wall 152 extends from the edge 166 to the lower side 160 of lower member 82. When assembled, the notch 190 may be aligned with the cavity 134 of the receptacle portion 114 (of upper member 80) so that flange 156 does not interfere with the end 128 of passage L1 when the end 128 is inserted therein. Notch 190 is optional and is not required in all examples. Thus, inlet 86 may comprise the port element 96, the notch 190, or a combination thereof. Thus, the inlet 86 includes any suitable means for coupling the respective passage (e.g., passage L1) to the nozzle 30—e.g., including any suitable fluid connectors, any suitable fasteners (e.g., such as ring clamps, clips, etc.), and/or the like.

Figure 6:
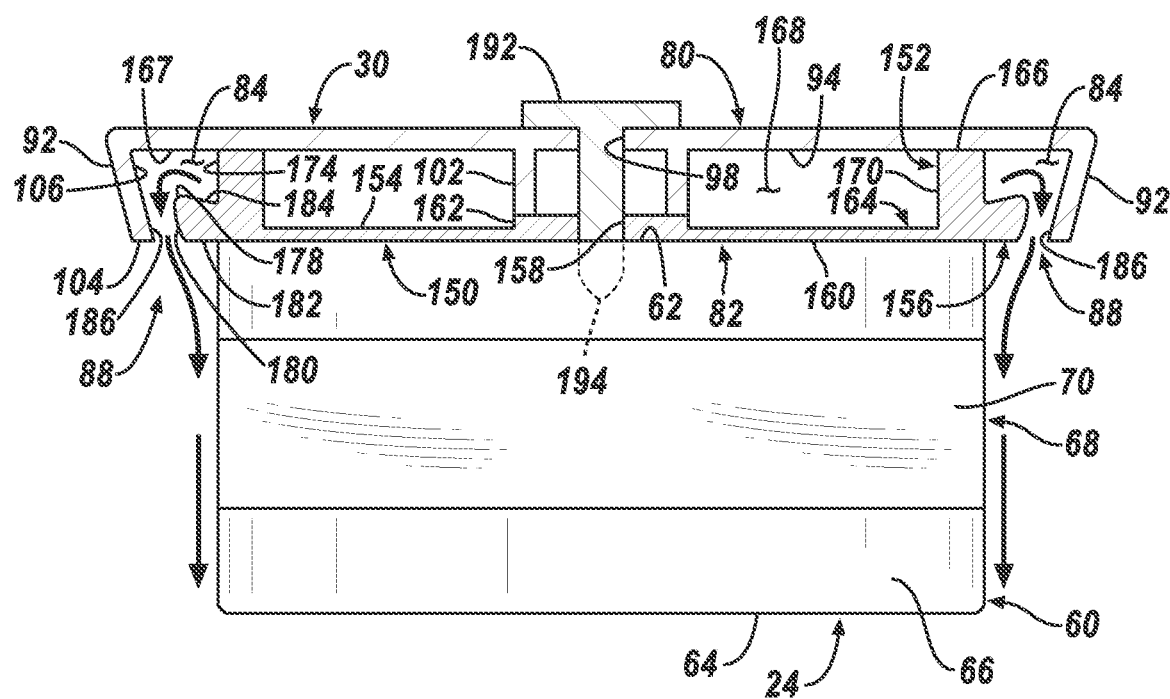
FIG. 6 is a sectional view of the nozzle carried by the sensor
Figure 7:
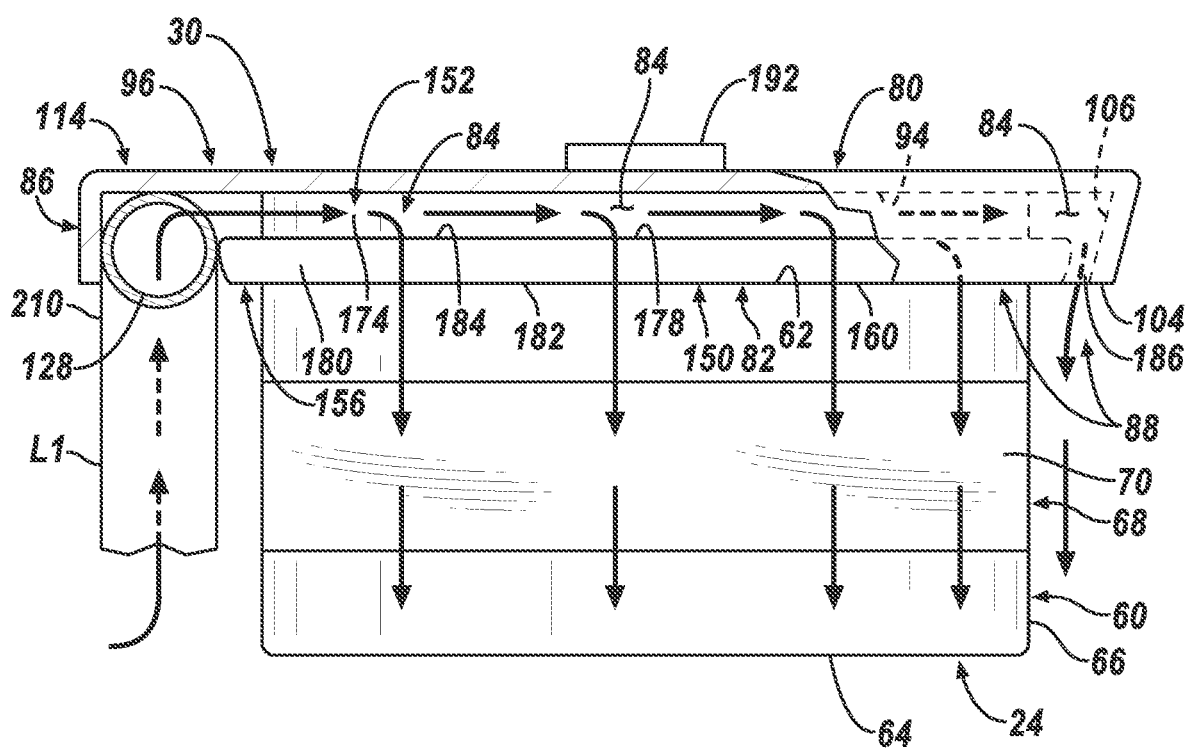
FIG. 7 is a cut-away view of the nozzle carried by the sensor further illustrating the exemplary fluid-flow pattern shown in FIG. 4.

According to at least one example, the shape of the nozzle 30 is circular—corresponding to the cylindrical shape of sensor 24. Thus, in this example, the base 90 (of upper member 80) is circular and the flange 92 and edge 104 are annular. Similarly, with respect to the corresponding lower member 82, the base 150 is circular and the wall 152 and flange 156 are annular. Accordingly, in at least one example, the passage 84 is annular—e.g., as the collective features that form the passage 84 are annular (e.g., features such as the inner surface 106, the periphery region 167, the outer surface 174, the channel 184, the edge surface 180, etc.). Further, as best shown in FIG. 6, in this example, a cross-section of the passage 84 may be L-shaped. Of course, this is merely one example.

An elliptically-shaped (and especially an annularly-shaped) passage 84 may promote an entrainment effect which is useful in removing debris from window 68. As used herein, debris should be broadly construed to include dirt, dust, sand, mud, pollen, insect or animal body parts or feces, pieces of rubbish or waste, ice, snow, food, other like contaminants, etc. The entrainment effect is a phenomenon that pertains to moving an unpressurized fluid based on the movement of a pressurized fluid resulting in an overall increase in fluid movement. More specifically, the unpressurized fluid near a moving (pressurized) fluid begins to move in the direction of the moving fluid—moving this unpressurized fluid can be dependent upon the shape of the outlet through which the pressurized fluid is directed. In the present case, the entrainment effect can cause an increase in fluid velocity as a result of the pressurized fluid moving through circumferential outlet 88. More particularly, unpressurized fluid that is located around the inner surface 106, around the edge surface 180, around the lower surface 182, etc. begins to move with the pressurized fluid delivered (from pumps 50 and/or 54 and) through outlet 88 thereby increasing the overall flow rate on the window 68 and improving debris removal. Thus, according to at least one example, a so-called air blade may comprise both compressed air delivered via passage L1 and unpressurized air located around the outlet 88.

The nozzle 30 further may comprise a fastener 192 which retains the upper and lower members 80, 82 to the sensor 24. For example, the fastener 192 may be located through both through-holes 98, 158 and into a blind hole 194 or other suitable attachment feature in the top 62 of shell 60. The term fastener should be construed broadly to include any device that suitably retains the nozzle 30 to sensor 24. In at least one example, the term fastener should be construed broadly to include any device that suitably retains the nozzle 30 to the top 62 of sensor 24. In some examples, the fastener 192 also may retain the orientation of the upper member 80 with respect to the orientation to the lower member 82; however, this is not required. Non-limiting examples of fastener 192 include one or more screws, bolts, nails, pins, clips, clamps, locks, a combination thereof, etc.

Coupling or mounting the nozzle 30 to the top 62 of sensor 24 may prevent the outlet 88 from becoming clogged (or at least partially clogged). For example, if the outlet 88 were directed upwardly, debris may fall into the outlet 88—e.g., after being removed from the window 68 of sensor 24. Further, by placing the nozzle 30 atop sensor 24, fluid flow pressure may be increased—e.g., as gravity may assist in the movement of the fluid. However, examples exist wherein the nozzle 30 may be located elsewhere relative to sensor 24.

Returning to FIG. 2, computer 22 of the sensor cleaning system 10 is shown electrically coupled to sensors 24-28, pumps 50, 54, and driving member 42. Computer 22 may be a single computer (or multiple computing devices—e.g., as described above, computer 22 may be shared physically and/or logically with other vehicle systems and/or subsystems). Computer 22 may comprise a processing circuit or processor 196 coupled to memory 198. For example, processor 196 can be any type of device capable of processing electronic instructions, non-limiting examples including a microprocessor, a microcontroller or controller, an application specific integrated circuit (ASIC), etc.—just to name a few. In general, computer 22 may be programmed to execute digitally-stored instructions, which may be stored in memory 198, which enable the computer 22, among other things: to actuate the driving member 42 to move a sensor (e.g., sensor 24) between a first or stowed position and a second or deployed position; to determine the presence of debris on any one of sensors 24-28; to selectively control fluid delivery to sensors 24-28 (e.g., selectively controlling which sensor(s) to clean and what type of fluid to deliver); to selectively control fluid delivery to the sensors 24-28 when the respective sensor is in a deployed position; to selectively control delivery of a gas to sensors 24-28; to determine whether the gas removed the debris; to determine when the debris is not removed by application of the gas; to selectively control delivery of a liquid to sensors 24-28; to determine whether the liquid removed the debris; to selectively repeat the delivery of gas and/or liquid to the sensors 24-28 when the debris remains; to repeat the delivery of gas and/or liquid a predetermined quantity of times before generating a diagnostic trouble code (DTC) for an authorized service technician; or to execute any combination of these or other instructions.

Memory 198 may include any non-transitory computer usable or readable medium, which may include one or more storage devices or articles. Exemplary non-transitory computer usable storage devices include conventional computer system RAM (random access memory), ROM (read only memory), EPROM (erasable, programmable ROM), EEPROM (electrically erasable, programmable ROM), as well as any other volatile or non-volatile media. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read. As discussed above, memory 198 may store one or more computer program products which may be embodied as software, firmware, or the like.

As also shown in FIG. 2, reservoir 52 of sensor cleaning system 10 may comprise one or more walls 200 which define an enclosed cavity 202 adapted to retain a first fluid. In at least one example, the first fluid is a liquid cleaning solution such as water, windshield washer fluid, or the like; however, this is not required (e.g., in other examples, the first fluid may be any suitable gas or other fluid).

Pump 50 may be located at least partially within the cavity 202 (e.g., at least partially submerged within the first fluid)—e.g., having an intake (not shown) which receives and pressurizes the first fluid and selectively delivers it to the nozzles 30-34 via one or more of passages L1-L3, as described more below. The pump 50 may be any suitable electronically-actuatable pump. Non-limiting examples include one or more positive displacement pumps (e.g., gear pumps, impeller pumps, plunger pumps, etc.), one or more velocity pumps (e.g., including jet pumps, jet valves, etc.), a combination thereof, or the like.

Pump 50 further may include one or more electronically-actuatable ports P1, P2, P3. In one example: when selectively actuated by computer 22, port P1 may provide the first fluid to nozzle 30 via passage L1; when selectively actuated by computer 22, port P2 may provide the first fluid to nozzle 32 via passage L2; and when selectively actuated by computer 22, port P3 may provide the first fluid to nozzle 34 via passage L3. This arrangement is merely an example. For instance, the pump 50 could be controlled to provide concurrently first fluid to any combination of nozzles 30-34 via a single port (e.g. such as port P1). Or in another example, the ports P1, P2, P3 could be embodied as computer-controlled valves which are located at any suitable position along respective passages L1, L2, L3—e.g., the ports P1, P2, P3 could be electronically-actuatable flow-control valves or the like.

According to at least one example, the reservoir 52 and pump 50 may be shared with other vehicle systems. For example, in one instance, the reservoir 52 and first pump 50 could be used to deliver the first fluid to the vehicle front windshield, vehicle rear windshield, vehicle headlamps, a combination thereof, or the like.

As discussed above, the second pump 54 may not require the use of a reservoir. Pump 54 may pressurize a second fluid (e.g., such as air or other gas) and selectively provide it to the nozzles 30-34 (e.g., via passages L4-L6, respectively) via port P4 (note: while a single port (P4) is shown with respect to pump 54, in other examples, pump 54 may comprise multiple ports similar to pump 50). In at least one example, second pump 54 also may include at least one electronically-actuatable pump such as a positive displacement pump or the like (including pump examples cited above). It should be appreciated that only two pumps 50, 54 are shown; however, any suitable quantity of pumps may be used to deliver a first or second fluid to the nozzles 30-34 so that debris may be removed from the vehicle sensors 24-28, as will be explained in greater detail below. For example, reservoir 52 may carry multiple pumps (or system 10 may comprise multiple reservoirs each having one or more pumps). Further, while the system 10 is shown near a front side S1 of vehicle 12, this is not required (e.g., elements of pumps 50, 54, reservoir 52, etc. may be located at or near front side S1, at or near a rear side S2 of vehicle 12, at or near a port side S3 of vehicle 12, or at or near a starboard side S4 thereof).

Figure 3:
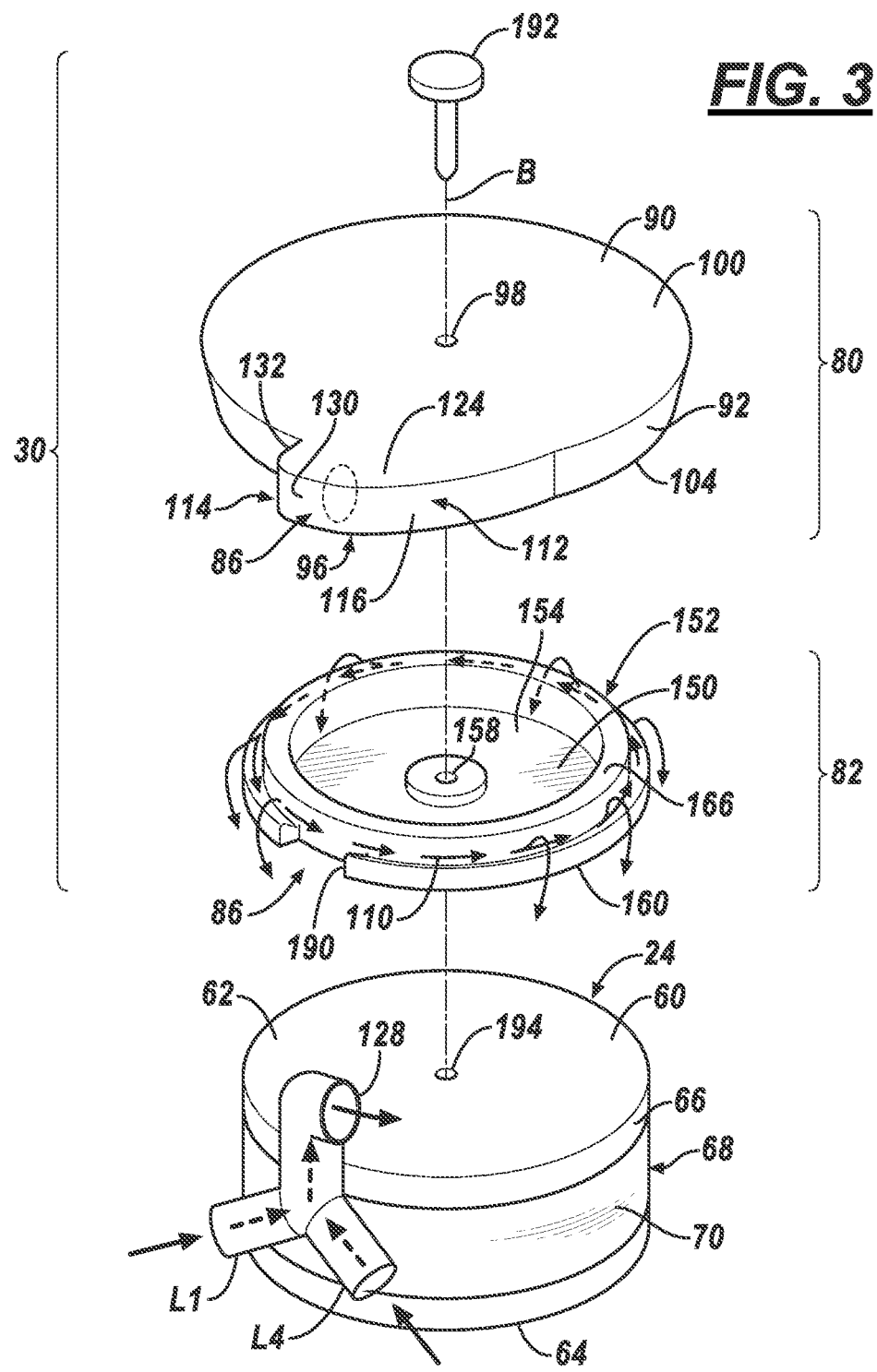
FIG. 3 is an exploded, perspective view of a sensor, a nozzle, and a portion of a supply passage for providing fluid to the nozzle for cleaning the sensor.
Figure 4:
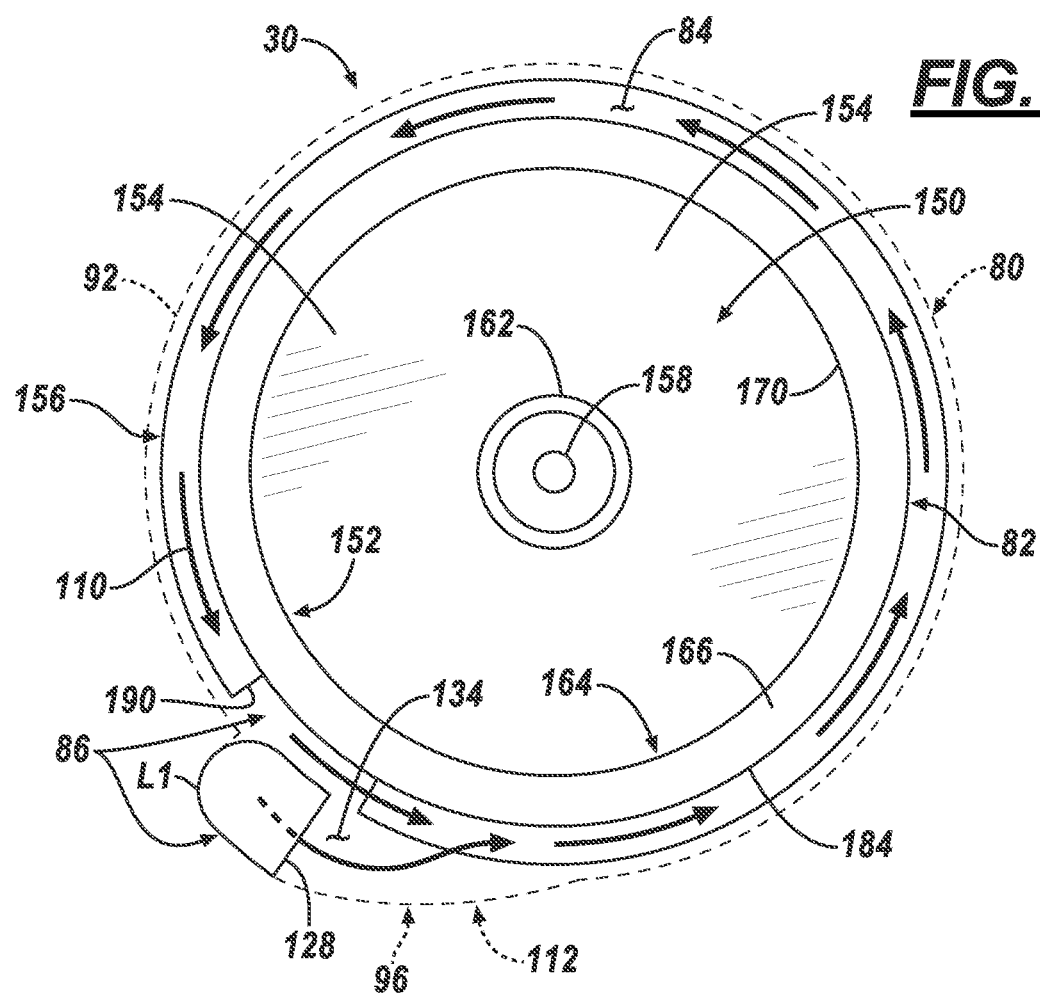
FIG. 4 is a sectional top view of the nozzle illustrating a fluid-flow pattern therein.
Figure 5:
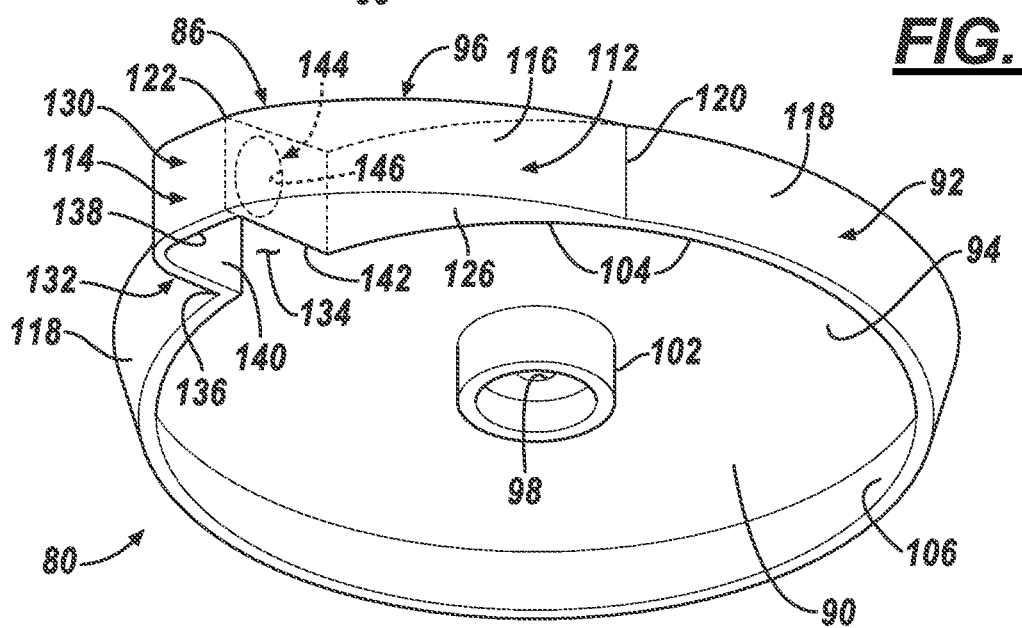
FIG. 5 is a perspective bottom view of a portion of the nozzle.

Passages L1-L6 may comprise any suitable tube, pipes, conduits, fittings, joints, couplers, valves, etc. adapted to deliver pressurized contents. They may be comprised of metal, plastic, and/or any suitable composite. As shown in FIG. 3, passage L4 may adjoin passage L1, and passage L1 may include an elbow region 210 that extends to nozzle 30. Thus, a first fluid may be delivered to nozzle 30 via passage L1, and a second fluid may be delivered to nozzle 30 via both passages L4 and an end portion of passage L1 (these passages being in fluid communication with one another). The elbow region 210 may comprise any suitable bend or turn which enables the end 128 of passage L1 to deliver fluid into nozzle 30, as described above. In at least one example, passages L1 and L4 form (or merge at) a Y-intersection; however, this is not required. Passages L2, L5 and passages L3, L6—which correspond to nozzles 32, 34, respectively—may be similarly arranged; therefore, this will not be described in greater detail.

While sensor assemblies 26-28 may comprise brackets 36, 38 (described above), this is not required. According to at least one example, one or more of sensor assemblies 26-28 could comprise a housing and driving member similar to the housing 40 and driving member 42 shown in the example of sensor assembly 16. In such examples, the respective housings and driving members may be identical; therefore, only one will be described.

Figure 8:
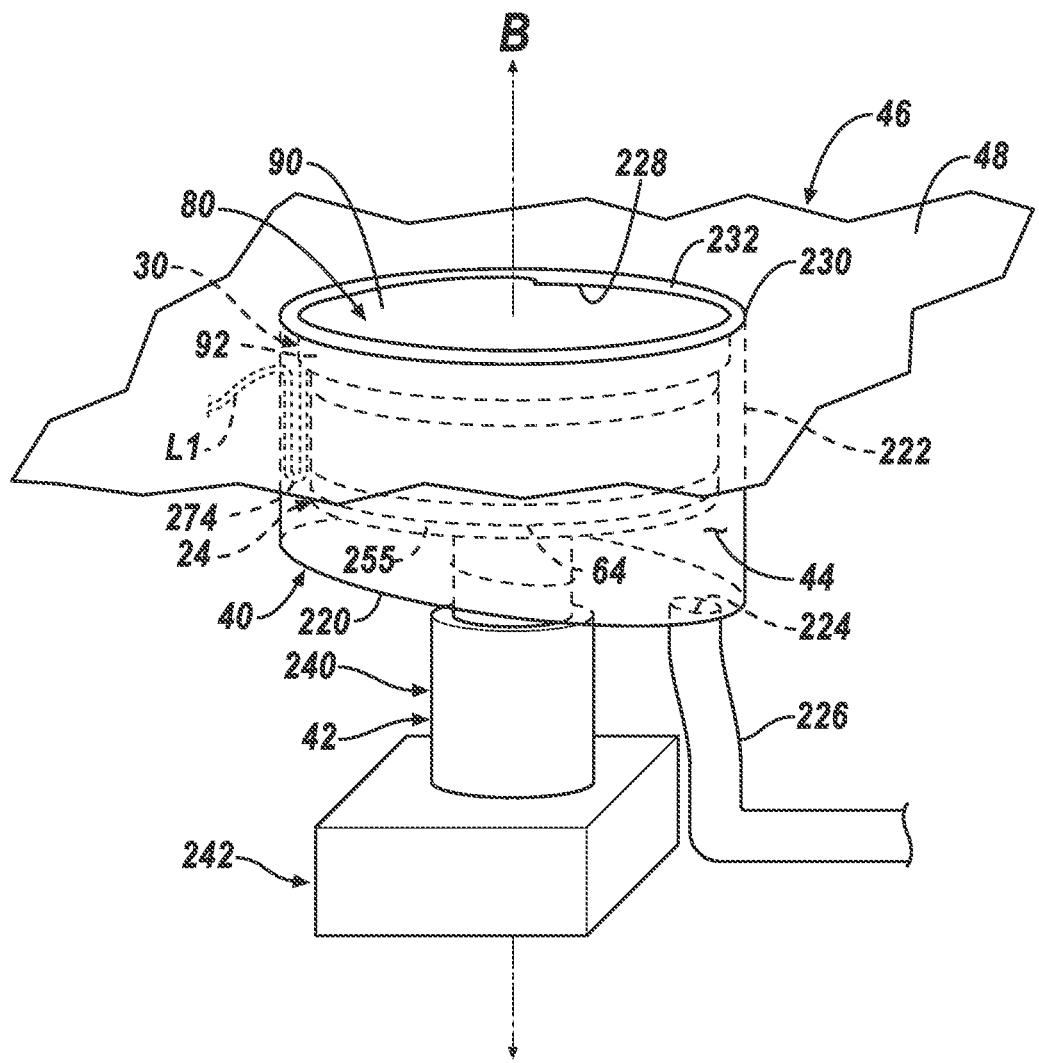
FIG. 8 is a cut-away view of a portion of the vehicle, illustrating the sensor assembly of FIG. 1A in a stowed position.
Figure 9:
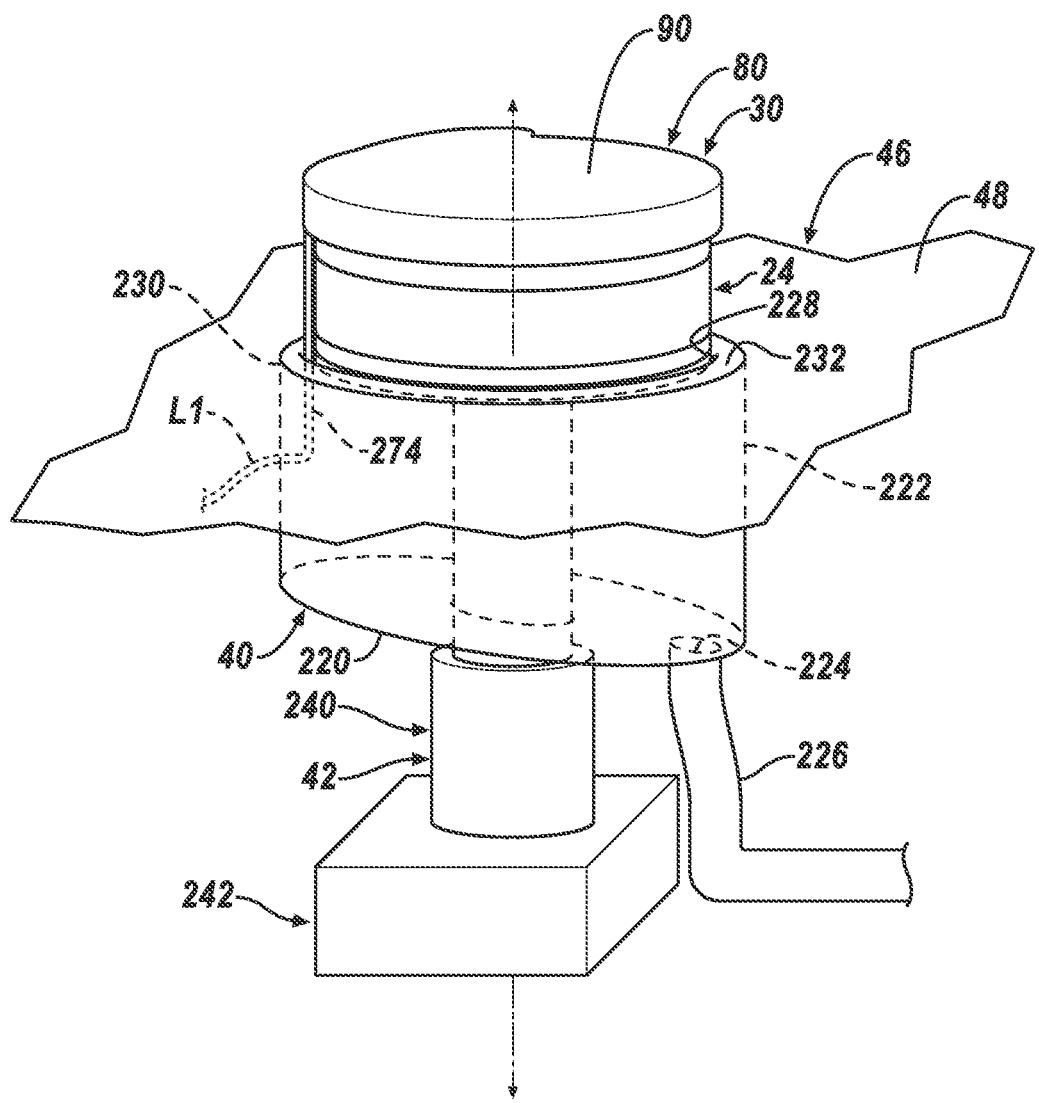
FIG. 9 is the same cut-away view, but illustrating the sensor assembly of FIG. 1A in a deployed position.
Figure 10:
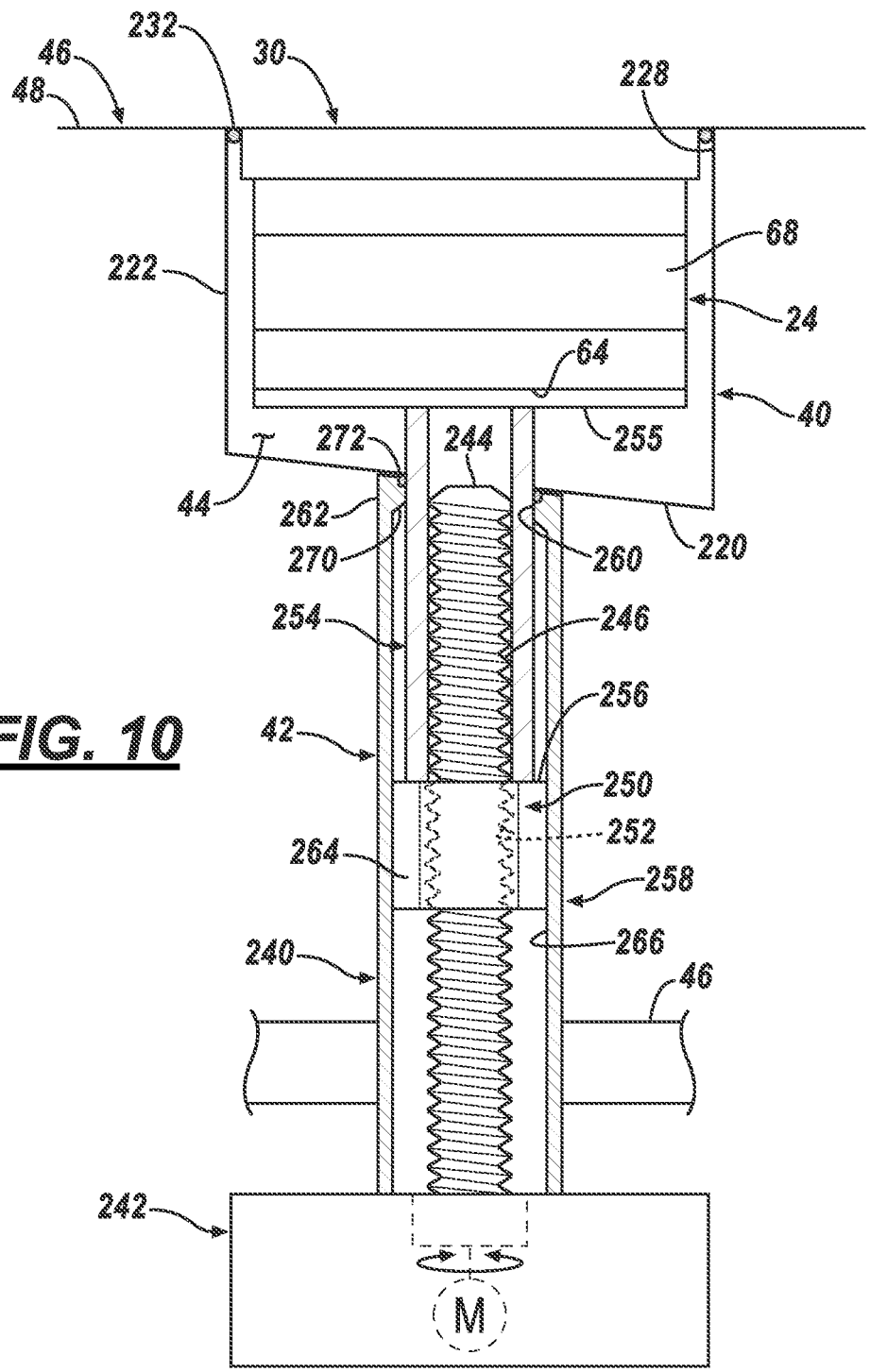
FIG. 10 is a partial sectional view of the sensor assembly illustrating a driving member for moving a sensor of the sensor assembly between the stowed and deployed positions.

As best shown in FIGS. 8-10, housing 40 may comprise a base 220 and one or more walls 222 axially extending from the base 220 to form cavity 44. In one example, wall 222 may be shaped as a right cylinder having a diameter slightly larger than the diameter of the upper member 80 of the nozzle 30; further, the housing 40 may be centered along axis B as well. Of course, this is merely an example and is not required. The base 220 may comprise a drain or opening 224 to a drain passage 226 so that the cavity 44 is in fluid communication with the passage 226. In this manner, liquid which may otherwise collect within the housing 40 may be drained therefrom; e.g., passage 226 may be open at an opposite end (not shown) so that fluid therein may drain to the ground below vehicle 12. According to one example, the fluid may be windshield washer fluid; however, passage 226 may facilitate the drainage of other fluids such as rain, melted snow or ice, etc. out of the housing 40 as well. In at least one example, the base 220 is sloped relative to the ground so that fluid within the housing 40 moves toward the opening 224 via gravity. As used herein, the term sloped should be construed broadly to include any surface that is inclined, angled, slanted, etc. relative to level ground, funneled, or the like.

The housing 40 may comprise an opening 228 at an end 230 that is opposite the base 220. In at least one example, the opening 228 has the same shape as upper member 80 (e.g., only slightly larger). Hence, opening 228 generally may be circular—e.g., being sized and shaped to accommodate the inlet 86 which may extend radially outwardly of base 90 (of upper member 80). Housing 40 may be carried by vehicle body 46, and opening 228 may be an opening within surface 48. In at least one example, opening 228 includes a circumferential, elastic seal 232 which facilitates a sealing engagement between the housing 40 and nozzle 30 (e.g., between the housing 40 and the flange 92 of upper member 80). In this manner, when the sensor 24 and nozzle 30 are in a stowed position (as shown in FIG. 8), fluids and debris may be at least partially inhibited from entering the cavity 44.

Driving member 42 may comprise any suitable device for moving the sensor 24 and nozzle 30 from the stowed position (FIG. 8) to a deployed position (FIG. 9). In at least one example, the driving member 42 axially displaces the sensor 24 and nozzle 30 along axis B, and further—in at least one example, the axial displacement is a vertical translation; however, this is not required. For example, the driving member 42 could translate the sensor 24 and nozzle 30 in other directions; the driving member 42 concurrently could rotate and translate the sensor 24 and nozzle 30; etc.

In at least one example, the driving member 42 includes a screw 240 and a motor 242 coupled to the screw 240. As best shown in FIG. 10, the screw 240 may be a lead screw and may comprise a shaft 244 (coupled to the motor 242—e.g., a stepper motor) having first threads 246, a nut 250 having second threads 252 that correspondingly engage the first threads 246, an inner sleeve 254 coupled to a sensor mount 255 which is coupled to the bottom 64 of the sensor 24, and an outer sleeve 258 which may be coupled the base 220 of the housing 40 and also the vehicle body 46. As illustrated, the inner sleeve 254 also may be coupled to an (upper) end 256 of nut 250—e.g., and may be formed in a single piece. The outer sleeve 258 may have an opening 260 at one end 262, and the inner sleeve 254 may be located at least partially within the outer sleeve 258—e.g., adapted to slidably move in relation thereto without interference. As used herein, the sensor mount 255 is any mechanical interface for carrying an imaging device (e.g., such as sensor 24)—e.g., including a bracket, fastener(s), etc.

An outer surface 264 of the nut 250 may have any suitable shape. In at least one example, the nut 250 is hexagonal; however, it could also be square, pentagonal, etc. An inner surface 266 of the outer sleeve 258 may have a shape that corresponds with the outer surface 264 of nut 250. Thus, in at least one example, the shape of surface 266 also may be hexagonal. An inner diameter of the outer sleeve 258 may be larger than an outer diameter of nut 250 so that the nut 250 may move slidably within the outer sleeve 258 without interference; however, the inner diameter may be suitably small enough to inhibit the nut 250 from rotating relative to the outer sleeve 258.

Furthermore, the sensor 24, nozzle 30, sensor mount 255, inner sleeve 254, and nut 250 (collectively, referred to as an example of a driven member) may be fixed or otherwise coupled to one another so that when the motor 242 rotates the shaft 244, the driven member moves relative to the outer sleeve 258 and shaft 244. The inner surface 266 of outer sleeve 258 may have a stop 270 (e.g., in FIG. 10, shown near end 262 of sleeve 258). In this manner, motor 242 may be actuated until the nut 250 abuts against the stop 270—the sensor 24 thereby being in the deployed position. In some examples, the end 262 of sleeve 258 may have a seal ring 272 to inhibit dust and debris from entering the outer sleeve 258; however, this is not required.

The motor 242 may be any suitable device for moving the driven member; and in the illustrated example, for providing angular rotation of the shaft 244. Non-limiting examples include brushed and brushless electric motors—e.g., including so-called servo and stepper motors. Motor 242 may include one or more gears, couplings, and/or other components (not shown) which may be used to engage the shaft 244. And computer 22 may be coupled to and used to control motor 242 in any suitable manner.

Thus, computer 22 may actuate the motor 242 in a first direction (e.g., to rotate shaft 244 counter-clockwise) and, as a result, move the sensor 24 and nozzle 30 from the stowed position (within the housing 40) to a deployed position (e.g., so that the window 68 of the sensor 24 is outside the housing 40—e.g., above the surface 48 of vehicle 12). As best shown in FIGS. 8-9, an excess length 274 of passage L1 may be provided in the stowed position (e.g., embodied as a loop or slack; see FIG. 8) so that when the sensor 24 and nozzle 30 are moved to the deployed position (FIG. 9), a sufficient length of passage L1 is available and does not create strain therein. Similarly, the computer 22 may actuate the motor 242 in a second, opposite direction (e.g., to rotate the shaft 244 clockwise) and, as a result, return the sensor 24 and nozzle 30 from the deployed position to the stowed position.

The above described components of the driving member 42 are merely one example. Other driving member examples may have different components, different arrangements, and/or operate in a different manner to move the sensor 24 and nozzle 30 between the stowed and deployed positions. Regardless, as used herein, the driven member comprises at least the sensor 24 and nozzle 30.

FIG. 11 illustrates one example of a computer-controlled process 1100 for cleaning sensor 24. The process begins with block 1110 that includes determining at computer 22 that the vehicle 12 is operating in or initiating an autonomous driving mode. In at least one example, this mode is a fully autonomous driving mode requiring imaging data from sensors 24, 26, and/or 28.

In block 1120 which follows, computer 22 may cause the driving member 42 to move the driven member from a stowed position to a deployed position. For example, as described above, the computer 22 may actuate motor 242 causing the screw 240 to translate vertically the sensor 24 and nozzle 30 upwardly through the opening 228. The computer 22 may execute a control loop to determine when the sensor 24 and nozzle 30 are in the deployed position (or e.g., the computer 22 may determine that the nut 250 has engaged the stop 270 by sensing back-electromotive force (EMF) in motor 242 or the like).

In block 1130, the computer 22 may actuate pump 54 after (or during) block 1120 to deliver a gaseous fluid to the nozzle 30. Consequently, the fluid may be delivered as an air-blade downwardly along the outer surface 70 of window 68. This actuation may occur during each deployment of sensor 24; or it may occur as a result of computer 22 detecting debris on window 68 using image processing techniques known in the art.

In block 1140 which follows, computer 22 may monitor and/or determine whether the window 68 of sensor 24 is clean of debris. In at least some examples, this monitoring or determining is similar to that described in block 1130 (e.g., using known techniques). When the window 68 is determined to be clean, the process 1100 may proceed to block 1150. And when the window 68 is determined to not be clean, the process may proceed to block 1170.

In block 1150, computer 22 may determine whether the vehicle 12 is exiting the autonomous driving mode. This may occur, e.g., during an ignition OFF event or at any other time in which a driver of vehicle 12 desires to assume control thereof. In block 1150, if the vehicle 12 is exiting the autonomous driving mode, then process 1100 proceeds to block 1160. If the vehicle 12 remains in the autonomous driving mode, then the process may loop back and repeat block 1140—e.g., and this looping back may occur repeatedly.

In block 1160, the computer 22 may actuate the motor 242 to move the sensor to the stowed position again, as described above. And thereafter, the process may end.

In block 1170 (which may follow block 1140 when the window 68 is not clean), the computer 22 may actuate pump 50 to deliver a different fluid to sensor 24. For example, computer 22 may cause a liquid such as window washing fluid to be delivered as a fluid-blade to window 68. Thereafter, process 1100 may loop back and repeat block 1140. This loop may occur repeatedly as well. In at least some examples, computer 22 may employ a counter, and when the counter reaches a threshold, the computer 22 may terminate dispensing liquid from reservoir 52 (e.g., to conserve washing fluid). In such instances, the process 1100 may terminate following block 1140—e.g., at least with respect that particular sensor 24. Thus, while process 1100 may end, other sensors individually may continue to operate in accordance with the process. In at least some examples, the vehicle 12 may determine to exit the fully autonomous driving mode—e.g., if inadequate sensor data is available.

The process shown in FIG. 11 and described above is merely one example. Any suitable fluid may be applied to sensor 24—e.g., including application of two fluids concurrently. Further, computer 22 may control pump 50 and/or pump 54 (or ports thereof) in any suitable manner to selectively control delivery of fluid to the nozzles 30, 32, 34.

In at least one example, the sensor (e.g., 24) may be cleaned while the sensor 24 and/or nozzle 30 are in the stowed position. For instance, according to one non-limiting example, block 1130 may occur prior to blocks 1110 and/or 1120.

Still other examples also exist. For example, the nozzle (20-23) could be coupled to the bottom 64 of the respective sensor—e.g., directing fluid upwardly along the side(s) 66 thereof. In this manner, the respective sensors may or may not have a dead zone.

According to another example, circumferential wall 152 could protrude from upper member 80 and abut against lower member 82 (e.g., inboard of flange 156). Still other examples exist as well.

Thus, there has been described a sensor cleaning system for a vehicle. The system may include a sensor assembly that includes a sensor, a fluid-delivery nozzle, a housing, and a driving member coupled to the sensor—e.g., to move the sensor (and/or nozzle) between a stowed position to a deployed position. The system further may include one or more pumps and passages to deliver a fluid to the nozzle which thereby may be used to clean the sensor.

In general, the computing systems and/or devices described may employ any of a number of computer operating systems, including, but by no means limited to, versions and/or varieties of the Ford SYNC® application, AppLink/Smart Device Link middleware, the Microsoft® Automotive operating system, the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX and iOS operating systems distributed by Apple Inc. of Cupertino, Calif., the BlackBerry OS distributed by Blackberry, Ltd. of Waterloo, Canada, and the Android operating system developed by Google, Inc. and the Open Handset Alliance, or the QNX® CAR Platform for Infotainment offered by QNX Software Systems. Examples of computing devices include, without limitation, an on-board vehicle computer, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The processor is implemented via circuits, chips, or other electronic component and may include one or more microcontrollers, one or more field programmable gate arrays (FPGAs), one or more application specific circuits ASICs), one or more digital signal processors (DSPs), one or more customer integrated circuits, etc. The processor may be programmed to receive imaging data, control vehicle pumps, control vehicle heaters, etc. Processing the data may include processing the video feed or other data stream captured by the sensors to determine the roadway lane of the host vehicle and the presence of any target vehicles. As described below, the processor instructs vehicle components to actuate in accordance with the sensor data. The processor may be incorporated into a controller, e.g., an autonomous mode controller.

The memory (or data storage device) is implemented via circuits, chips or other electronic components and can include one or more of read only memory (ROM), random access memory (RAM), flash memory, electrically programmable memory (EPROM), electrically programmable and erasable memory (EEPROM), embedded MultiMediaCard (eMMC), a hard drive, or any volatile or non-volatile media etc. The memory may store data collected from sensors.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The terms upward, upwardly, downward, downwardly, etc. are relative terms meant for purposes of explanation only and should not be construed as limitations.

The invention claimed is:
1. An assembly, comprising:
a housing having a cavity sized for a sensor, the housing comprising an opening at a first end, and a housing base having a drain at an opposite end;
a nozzle coupled to a top of the sensor;
a sensor mount; and
a driving member coupled to the mount to move the mount, through the opening, between a stowed position and a deployed position.

2. The assembly of claim 1, wherein the nozzle has an annular shape, wherein the nozzle is positioned above the base so that fluid dispensed by the nozzle exits the cavity via the drain.

3. The assembly of claim 1, wherein the driving member comprises a screw coupled to a motor.

4. The assembly of claim 3, wherein the driving member includes an outer sleeve and an inner sleeve that is coupled to the mount and, when the mount moves between the stowed and deployed positions, the inner sleeve moves relative to the outer sleeve.

5. The assembly of claim 1, wherein the housing base is sloped toward the drain.

6. The assembly of claim 1, further comprising the sensor, wherein the sensor also is coupled to the mount.

7. The assembly of claim 1, wherein the nozzle is sized to move through the opening, wherein the nozzle comprises:

a first member comprising an annular first flange extending radially-inwardly from a first nozzle base; and a second member having an annular second flange extending radially-outwardly from a second nozzle base, the first and second flanges forming a circumferential passage and an at least partially circumferential outlet.

8. The assembly of claim 7, wherein at least a portion of the first flange is parallel to at least a portion of the second flange.

9. The assembly of claim 7, wherein a width of the outlet is uniform.

10. The assembly of claim 7, wherein the first or second member comprises a circumferentially-extending wall protruding from the respective first or second nozzle base, wherein the wall is located inboard of the second flange, wherein an edge of the wall abuts the respective second or first nozzle base.

* * * * *